(12) United States Patent
Nagamura et al.

(10) Patent No.: US 6,197,955 B1
(45) Date of Patent: Mar. 6, 2001

(54) PRODUCTION OF STAUROSPORINE DERIVATIVE USING ACID ISOMERIZATION

(75) Inventors: Satoru Nagamura, Yamaguchi; Hidenori Aoki; Mitsutaka Kino, both of Hofu; Toshimitsu Takiguchi, Gotemba, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/466,903

(22) Filed: Dec. 20, 1999

(30) Foreign Application Priority Data

Dec. 22, 1998 (JP) .................................................. 10-364369

(51) Int. Cl.[7] .................................................. C07D 498/22
(52) U.S. Cl. ........................................... 540/545; 540/546
(58) Field of Search ...................................... 540/545, 546

(56) References Cited

U.S. PATENT DOCUMENTS 4,935,415    6/1990  Nakano et al. ..................... 514/211
5,344,926  * 9/1994  Murakata et al. ................... 540/545

FOREIGN PATENT DOCUMENTS 0 383 919    8/1990  (EP) .

OTHER PUBLICATIONS

Angewandte Chemie International edition, vol. 38, No. 4 (1999), pp. 549–552.

* cited by examiner

Primary Examiner—Mukund J. Shah
Assistant Examiner—Pavanaram K Sripada
(74) Attorney, Agent, or Firm—Fitzpatrick, Cella, Harper & Scinto

(57) ABSTRACT

A staurosporine derivative with anti-cancer activity and anti-bacterial activity is produced by acidifying a solution containing staurosporine to isomerize staurosporine to its desired derivative, whereby the derivative is recovered from the acidified solution.

8 Claims, No Drawings

PRODUCTION OF STAUROSPORINE DERIVATIVE USING ACID ISOMERIZATION

BACKGROUND OF THE INVENTION

1. Field of the Invention

The present invention relates to a process for producing UCN-01 from a solution containing UCN-02 in an efficient and simple manner without complicated steps.

2. Brief Description of the Background Art

UCN-01 is a well-known compound with anti-cancer activity and anti-bacterial activity, having the structure represented by the following formula (II).

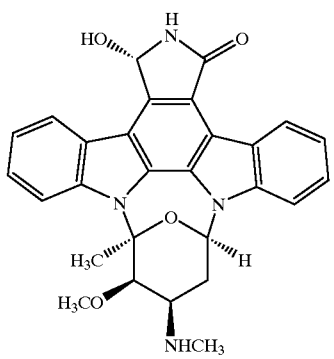

(II)

The following processes for producing UCN-01 are known:

(1) Japanese Published Unexamined Patent Application 87/220196 provides a fermentation method comprising culturing a microorganism of genus Streptomyces with an ability to generate UCN-01 in a culture medium and harvesting the generated UCN-01;

(2) WO 89/07105 provides a method comprising three-step chemical synthesis of UCN-01 from staurosporine represented by the following formula (III).

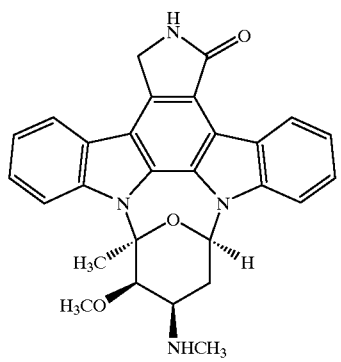

(III)

Staurosporine is a potent inhibitor of Protein Kinase C and can be readily obtained from Streptomyces sp. Staurosporine is also commercially available, for instance, from Fermentek Corp. of Jerusalem, Israel.

(3) Japanese Published Unexamined Patent Application 94/9645 provides a method comprising oxidizing staurosporine in a solution comprising dimethyl sulfoxide and an aqueous alkali solution to a racemic mixture of UCN-02 represented by the following formula (I):

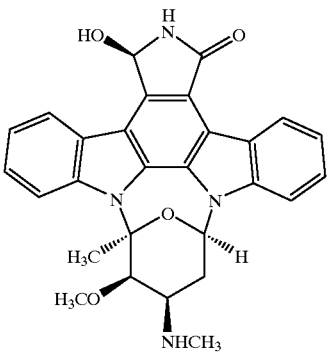

(I)

and a steric isomer thereof, UCN-01 represented by the formula II above, and recovering UCN-01 by column chromatography using a carrier such as a synthetic adsorbent (for example, Diaion HP-20SS manufactured by Mitsubishi Chemical Industries, Co., Ltd.) and silica gel.

However, these methods are disadvantageous in that the culture titer by the fermentation of method (1) is low; the yield of UCN-01 resulting from the chemical synthesis of method (2) is low because 3 steps are required; and the recovery of UCN-01 is low in the column chromatography purification step of method (3) because UCN-02 must be removed as an impurity. Thus, known procedures are very complicated and are not applicable to large scale commercial synthesis.

SUMMARY OF THE INVENTION

The present invention relates to a process for producing UCN-01 in an efficient and simple manner.

More specifically, the present invention provides a process for producing UCN-01, comprising acidifying a solution containing UCN-02 so as to isomerize UCN-02 to UCN-01, and recovering UCN-01 from the resulting acidified solution.

DETAILED DESCRIPTION OF THE INVENTION

The process for producing UCN-01 according to the present invention firstly requires only a solution containing UCN-02. Using such a solution, in conformity with the present invention, highly purified UCN-01 can be produced at an excellent efficiency in a simple manner.

Any solution containing UCN-02 may be used as the solution containing UCN-02 in accordance with the present invention. Suitable solutions containing UCN-02 include, for example, a solution obtained by oxidizing staurosporine in a solution comprising dimethyl sulfoxide and an aqueous alkali solution as discussed in aforementioned Japanese Published Unexamined Patent Application 94/9645.

Solutions containing UCN-02 may contain UCN-01. Therefore, when the solution containing both of UCN-01 and UCN-02, which is obtained by the process for producing UCN-01, is treated by the process of the present invention, the solution containing UCN-01, which consists of both of UCN-01 changed from UCN-02 and UCN-01 existing in the original solution, is obtained, and UCN-01 can be obtained in high yield without separation of UCN-02 from the solutions, The reaction to isomerize UCN-02 to UCN-01 can be carried out by adding water so that the concentration of water in the solution is preferably 50 v/v % or more, more preferably 90 v/v % or more, and adjusting the solution to preferably pH 5 or less, more preferably pH 1 to 3, further more preferably pH 2 to 2.5.

The concentration of UCN-02 in the reaction mixture is preferably 25 g/L or less, more preferably 5 to 10 g/L. When UCN-01 is contained in the reaction solution, the combined concentration of UCN-01 and UCN-02 in a reaction mixture is adjusted to the aforementioned concentration.

Acids to adjust pH include, among others, acetic acid, hydrochloric acid, sulfuric acid, trifluoroacetic acid, methanesulfonic acid, trifluoromethanesulfonic acid, p-toluenesulfonic acid and xylenesulfonic acid. Further, hydrochloric acid or sulfuric acid is preferably used, and hydrochloric acid is more preferably used.

The reaction temperature is 0 to 50° C., preferably 20 to 30° C.; and the reaction time is 1 to 24 hours.

When the reaction is complete, the reaction mixture is adjusted to pH 7 or more, whereby UCN-01 is precipitated from the reaction mixture. The precipitate of UCN-01 is separated from the reaction mixture in a conventional manner such as a filtration.

The invention is now described in detail in the following examples.

EXAMPLES 1–6

A solution containing UCN-01 and UCN-02 was prepared by dissolving staurosporine (1.0 g; 2.1 mmol) in 100 ml of dimethyl sulfoxide, followed by addition of 10 ml of 0.3 mol/L sodium hydroxide, and then stirring the resulting mixture at room temperature for 8 hours. The UCN-02/UCN-01 ratio in the solution was 14.2%.

Water (33 ml) was added to the solution to dilute the solution; and the resulting dilution was passed through a column (25 ml volume) packed with Diaion SP-207 manufactured by Mitsubishi Chemical Industries, Co., Ltd.

After the solution was passed through the column, SP-207 was treated sequentially with 25 ml of a 70% dimethyl sulfoxide solution, 75 ml of water, and 125 ml of an aqueous 0.02 mol/L hydrochloric acid solution, followed by elution of UCN-01 and UCN-02 with an aqueous 60% acetone solution containing 0.005 mol/L hydrochloric acid.

The resulting elution was concentrated by two-fold to remove acetone. Then, by using (1) 1 mol/L hydrochloric acid, (2) 1 mol/L sulfuric acid, (3) 1 mol/L trifluoroacetic acid, (4) 1 mol/L methanesulfonic acid, (5) 1 mol/L p-toluenesulfonic acid, or (6) 1 mol/L xylenesulfonic acid, the resulting solution was adjusted to pH 2.2 and agitated overnight at room temperature, to isomerize UCN-02 to UCN-01. The UCN-02/UCN-01 ratio in each of these solutions are shown in Table 1.

By adjusting these solutions to pH 8.5 by using aqueous 1 mol/L sodium hydroxide and subsequently filtering the resulting solution, UCN-01 was recovered. The recovered weight and recovery are also shown in Table 1.

TABLE 1

| Acid (1 mol/L) | UCN-02/UCN-01 (%) | Recovered weight (g) | Recovery (%) |
| --- | --- | --- | --- |
| 1. Hydrochloric acid | 3.7 | 0.8 | 84 |
| 2. Sulfuric acid | 4.0 | 0.7 | 73 |
| 3. Trifluoroacetic acid | 5.0 | 0.7 | 74 |

TABLE 1-continued

| Acid (1 mol/L) | UCN-02/UCN-01 (%) | Recovered weight (g) | Recovery (%) |
| --- | --- | --- | --- |
| 4. Methanesulfonic acid | 4.7 | 0.8 | 77 |
| 5. p-Toluenesulfonic acid | 4.0 | 0.7 | 74 |
| 6. Xylenesulfonic acid | 3.5 | 0.8 | 75 |

Example 7

UCN-01 prepared under the conditions in Example 1 was dissolved in 200 ml of chloroform, and the solution was subsequently concentrated to 7 ml. UCN-01 was crystallized from the solution, and 0.7 g of UCN-01 crystal (purity 99%) was recovered.

The content of UCN-02 in the recovered UCN-01 crystal was 0.2%.

What is claimed is:

1. A process for producing a staurosporine derivative, comprising the steps of acidifying a solution containing a compound represented by formula (I):

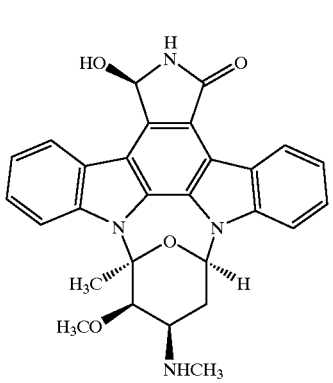

(I)

to isomerize said compound according to formula (I) to form a compound represented by formula (II):

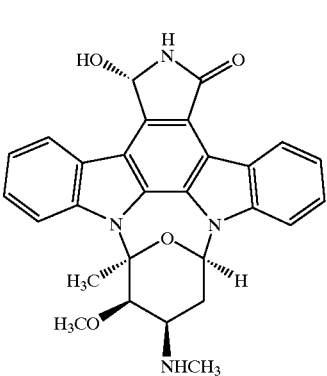

(II)

and recovering said compound according to formula (II) from the acidified solution.

2. The process according to claim 1, wherein the solution is acidified by using an acid selected from acetic acid, hydrochloric acid, sulfuric acid, trifluoroacetic acid, methanesulfonic acid, trifluoromethanesulfonic acid, p-toluenesulfonic acid and xylenesulfonic acid.

3. The process according to claim 1, wherein the acidified solution is below pH 5.

4. The process according to any of claims 1–3, wherein the solution containing the compound according to formula (I) also contains the compound according to formula (II).

5. The process according to any of claims 1–3, wherein isomerization occurs at a reaction temperature of 0 to 50° C.

6. The process according to claim 4, wherein isomerization occurs at a reaction temperature of 0 to 50° C.

7. The process according to any of claims 1–3, wherein isomerization occurs at a reaction temperature of 20 to 30° C.

8. The process according to claim 4, wherein isomerization occurs at a reaction temperature of 20 to 30° C.

* * * * *